(12) United States Patent
Wloch et al.

(10) Patent No.: US 10,669,222 B2
(45) Date of Patent: Jun. 2, 2020

(54) PROCESS FOR ENRICHING ENANTIOMERS FROM AN ENANTIOMER MIXTURE

(71) Applicant: BASF SE, Ludwigshafen am Rhein (DE)

(72) Inventors: Sebastian Wloch, Ludwigshafen am Rhein (DE); Gunnar Heydrich, Ludwigshafen am Rhein (DE); Matthias Rauls, Ludwigshafen am Rhein (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/338,633

(22) PCT Filed: Oct. 5, 2017

(86) PCT No.: PCT/EP2017/075309
§ 371 (c)(1),
(2) Date: Apr. 1, 2019

(87) PCT Pub. No.: WO2018/065509
PCT Pub. Date: Apr. 12, 2018

(65) Prior Publication Data
US 2020/0039904 A1    Feb. 6, 2020

(30) Foreign Application Priority Data
Oct. 6, 2016 (EP) .................... 16192655

(51) Int. Cl.
*C07C 29/78* (2006.01)
*C07C 29/17* (2006.01)
*B01D 9/00* (2006.01)

(52) U.S. Cl.
CPC ............. *C07C 29/78* (2013.01); *B01D 9/004* (2013.01); *B01D 9/0013* (2013.01); *C07C 29/172* (2013.01)

(58) Field of Classification Search
CPC ....... C07C 29/78; C07C 29/172; B01D 9/004; B01D 9/0013
See application file for complete search history.

(56) References Cited

U.S. PATENT DOCUMENTS 7,820,860 B2    10/2010    Seidel-Morgen-Stern et al.
7,868,211 B2    1/2011    Rauls et al.
(Continued)

FOREIGN PATENT DOCUMENTS

EP          1924540 A2       5/2008
WO    WO-2007023109 A1      3/2007
(Continued)

OTHER PUBLICATIONS

Rodrigo et al. ("Online Monitoring of Preferential Crystallization of Enantiomers", Chirality, 2004, vol. 16, pp. 499-508).*

(Continued)

*Primary Examiner* — Rosalynd A Keys
(74) *Attorney, Agent, or Firm* — Faegre Drinker Biddle & Reath LLP (57) ABSTRACT

The present invention relates to a process for enriching enantiomers from an enantiomer mixture by a fractionating melt crystallization in a melt crystallization apparatus. The invention specifically relates to a process for producing an enantiomer-enriched chiral terpene, in particular of D/L-Isopulegol. The process comprises:
i) a crystallization step to obtain a crystallizate and a mother melt and removal of the mother melt from the crystallizate to afford a mother melt fraction;
ii) sweating of the crystallizate obtained in step i) to afford a molten sweating fraction and
iii) subsequent melting of the sweated crystallizate to afford a molten crystallizate fraction,
(Continued)

wherein the optical rotation at least of the sweating fraction is determined online using a polarimeter and the changeover from step ii) to step iii) is controlled online by means of at least one control unit.

20 Claims, 3 Drawing Sheets

(56) References Cited

U.S. PATENT DOCUMENTS

| | | |
|---|---|---|
| 10,195,167 B2 | 2/2019 | Wikstrom et al. |
| 10,301,244 B2 | 5/2019 | Schelwies et al. |
| 2008/0214877 A1 | 9/2008 | Rauls et al. |

FOREIGN PATENT DOCUMENTS

| | | |
|---|---|---|
| WO | WO-2007023129 A2 | 3/2007 |
| WO | WO-2018065509 | 4/2018 |

OTHER PUBLICATIONS

International Search Report for PCT/EP2017/075309 dated Dec. 21, 2017.
Written Opinion of the International Searching Authority for PCT/EP2017/075309 dated Dec. 21, 2017.
Lorenz, H. et al., "Application of Preferential Crystallization to Resolve Racemic Compounds in a Hybrid Process", Chirality, 2006, vol. 18, pp. 828-840.

* cited by examiner

PROCESS FOR ENRICHING ENANTIOMERS FROM AN ENANTIOMER MIXTURE

CROSS-REFERENCE TO RELATED APPLICATIONS

This application is a national stage application (under 35 U.S.C. § 371) of PCT/EP2017/075309, filed Oct. 5, 2017, which claims benefit of European Application No. 16192655.5, filed Oct. 6, 2016, both of which are incorporated herein by reference in their entirety.

The present invention relates to a process for enriching enantiomers from an enantiomer mixture by a fractionating melt crystallization in a melt crystallization apparatus. The invention specifically relates to a process for producing an enantiomer-enriched chiral terpene, in particular of D/L-Isopulegol.

With the exception of optical activity enantiomers have identical physical properties. Accordingly, mixtures of two enantiomers cannot be separated with most customary process engineering separating operations, for example distillation which is based on differences in boiling points. The separating processes for enantiomer separation or enrichment are often more complex and costly. One customary method is separation by chromatographic means by DC, GC or HPLC, wherein a chiral complexing partner forms the stationary phase.

For many active pharmaceutical ingredients the focus is on biochemical racemate separation. Since enzymes often convert substrates enantioselectively these or corresponding microorganisms are employed which metabolize the one enantiomer while the desired enantiomer remains preserved.

However, enantiomers can generally be separated more simply and cost-effectively by crystallization. One known method of racemate separation is so-called preferential or preferred crystallization. This process allows resolution of racemic substance mixtures provided that so-called conglomerate-forming systems, i.e. systems where the enantiomers are immiscible in the solid phase, are concerned.

When the starting mixture is enriched in one enantiomer in excess of the eutectic composition—for instance by synthesis from optically active starting compounds or by an upstream chromatography step—then enantioselective crystallization is possible. This affords a crystallizate of the enriched enantiomer and a mother liquor having the eutectic composition of the enantiomers.

Thus, WO 2007/023109 discloses a process for producing enantiomer- and/or diastereomer-enriched isopulegol by melt crystallization. The process provides enantiomer enrichment under simple apparatus and process engineering conditions in the absence of solvents and without addition of further auxiliary substances, for example crystallization nucleators.

In a melt crystallization the liquid melt of the mixture to be separated is charged into a crystallization apparatus. A crystal layer of the desired target product forms on cooled surfaces cooled below the melting point of the starting mixture. Undesired byproducts substantially remain in the mother melt. The mother melt is discharged thus achieving a first purification. A further purification can be effected by so-called sweating; here the temperature of the crystal layer is raised to just below the melting point via the cooling surfaces. A portion of the crystal layer at the interface with the remaining mother melt is thus incipiently melted and displaces the impurified mother melt. In addition this releases mother liquor trapped in the crystal. The molten sweating fraction is discharged; this achieves a further purification of the remaining crystallizate. Once the sweating is complete the remaining crystal layer is melted off. The switching point from sweating to melting is of great importance. If the sweating duration is too short the desired purity of the multicrystalline as it is not achieved. If the sweating duration is too long the desired purity is achieved but an unnecessarily large amount of the pure target product ends up in the sweating fraction. Active control of the switching point is yet more important since the progress of a melt crystallization is never completely reproducible despite unchanged operating parameters, particularly when high purities of the target product are targeted.

EP 1 924 540 A1 describes a process for racemate separation in compound-forming systems where initially a fraction enriched in one enantiomer is generated from a racemic mixture, for example by chromatography, in order in a second step to seed said fraction with the desired enantiomer and to enrich it from a solvent by preferred crystallization. The monitoring of the individual process steps may be effected inter alia by polarimetric measurements, preferably in combination with other measures, for example density measurement. This monitoring is said to allow ascertainment of the point at which the crystallization of the desired enantiomer must be discontinued. Specifically described is the crystallization of mandelic acid from an aqueous solution, wherein the composition of the solution is monitored by the combined online polarimetry and online density measurement.

Lorenz, H., Polenske, D. and Seidel-Morgenstern, A., Chirality, 18: 828-840 (2006) describes, similarly to EP 1 924 540 A1, the application of combined online polarimetry and online density measurement for monitoring of a preferred crystallization.

In the described publications an online polarimeter is used in the preferred crystallization to test the correct thermodynamic phase region in order to be able to crystallize-out the desired component. Application in the field of melt crystallization is not mentioned.

It has now been found that in the enrichment of an enantiomer from an enantiomer mixture by a fractionating melt crystallization a high enrichment of the desired enantiomer is achieved in particularly efficient fashion when the optical rotation of at least the sweating fraction is determined online by means of a polarimeter and the changeover from step ii) to step iii) is controlled online by means of at least one control unit. This additionally makes it possible to achieve a very readily reproducible enrichment coupled with a high optical purity of the desired enantiomer.

The present invention accordingly relates to a process for enriching an enantiomer from an enantiomer mixture by a fractionating melt crystallization in a melt crystallization apparatus, comprising i) a crystallization step to obtain a crystallizate and a mother melt and removal of the mother melt from the crystallizate to afford a mother melt fraction;

ii) sweating of the crystallizate obtained in step i) to afford a molten sweating fraction and a sweated crystallizate, and iii) subsequent melting of the sweated crystallizate to afford a molten crystallizate fraction, wherein the optical rotation at least of the sweating fraction is determined online using a polarimeter and the changeover from step ii) to step iii) is controlled online by means of at least one control unit.

The terms "determine online" and "control online" are in each case to be understood as meaning in principle an online processing operation which may comprise both the execution of tasks with interaction of the user (dialog processing) or else without user dialog (stack processing) via a common communication network. In particular online processing comprises execution of a command sequence in the context of a communication network with automatic transfer of data, optionally storage of the data (for later further processing or documentation) and/or immediate further processing of the data.

In the context of the present invention the term "determine online" is to be understood as meaning that in the process the optical rotation of the respective fraction, but at least the optical rotation of the sweating fraction, is continuously captured as a measured variable by means of a polarimeter, preferably without withdrawing a sample from the system.

The term "control online" is here and in the following to be understood as meaning the transfer of data and/or control variables, here the optical rotation of the respective fraction, between sensors, here the polarimeter, and actuators by means of an active connection via the common communication network.

According to the invention in step (c) the actual value of the optical rotation of the sweating fraction is determined online/inline.

In the context of the present invention the term "determined inline" is used synonymously with the term "determined online" and means that the optical rotation in the process is captured continuously, preferably without withdrawing a sample from the running process.

In the present control task, therefore, the optical rotation of the sweating fraction is specially captured online/inline as a measured value by means of a polarimeter, the accompanying value of the enantiomeric excess (EE value), which may be determined online from the optical rotation for example using a preprepared calibration curve, is optionally determined online and the change from step ii) to step iii) is controlled online by means of a control unit.

It is possible in principle to employ any melt crystallization apparatuses which function based on the formation of crystals on cooled surfaces. The process according to the invention may be performed as a dynamic process or a static process or as a combination of these two processes. Static melt crystallizations are preferred. In the static processes the liquid phase is moved only by free convection while in the dynamic processes the crystallization is performed with forced convection of the liquid phase. This may be effected through a forced flow in fully flooded heat exchangers or through application of a trickle film onto a cooled wall.

It is preferable when the melt crystallization is performed as a layer crystallization, in particular as a static layer crystallization on cooled surfaces or as a falling film crystallization. The melt crystallization apparatus is preferably configured as a falling film crystallizer or as a plate crystallizer.

Accordingly, the process according to the invention may also be performed in the form of a dynamic layer crystallization. In the context of a preferred embodiment this variant is performed in tube bundle heat exchangers, such as are described in G. F. Arkenbout, Melt Crystallization Technology, Lancater/PA, Technomic Publ. Co., 1995 (chapt. 6.2). Melt and coolant are conducted along the inner and outer walls of the heat exchanger in the form of a trickle film for example. An apparatus of this type allows for easier removal of the obtained crystallizate from the mother melt/the obtained sweating fractions by simple discharging under the action of gravity and without a need for further stirring means other than a circulation pump.

The liquid melt of the mixture to be separated is charged into the melt crystallization apparatus typically at a temperature, discernible from the melt diagram, above the melting point of the pure enantiomer. To perform a dynamic layer crystallization, the liquid melt of the mixture to be separated is charged and passed by pumped circulation through the cooled tube bundle heat exchanger. In the static layer crystallization preferred in accordance with the invention the liquid melt of the enantiomer mixture to be separated/enriched is charged into the crystallization apparatus which has coolable surfaces, for example in the form of cooled plates or tubes optionally equipped with fins.

The cooled surfaces are cooled to below the melting point of the starting mixture; after a certain supercooling a crystal layer comprising the desired enantiomer is formed on the surfaces. To achieve an advantageous crystallization result the reduction in the refrigerant temperature is preferably chosen such that over a period of about 5 h to about 24 h, preferably over about 7 h to about 19 h, a crystal layer having a thickness of about 1 mm to about 50 mm, preferably about 5 mm to about 30 mm, is formed. The coolant temperatures required therefor are generally about 2 K to about 32 K, preferably about 4 K to about 15 K, below the respective melt temperature.

The undesired enantiomer and any other impurities substantially remain in the mother melt. The melt is cooled further to a certain end temperature. The mother melt then still remaining is discharged. A certain amount of impurified mother melt remains on the crystal layer and may in some cases also be trapped in the crystals. For further purification the process according to the invention provides for a sweating step. Here, the temperature of the crystal layer is increased to just below the melting point via the cooling surfaces. A portion of the crystal layer at the interface with the remaining mother melt is thus incipiently melted and displaces the impurified mother melt. In addition, the mother liquor trapped in the crystal is released. Furthermore pores in the crystal layer still comprising combined mother melt may be opened. This achieves a further purification of the remaining crystallizate. Advantageous heat transfer medium temperatures are in the range from about 0.1 K to about 15 K below the melting point of the enantiomer mixture used for crystallization in each case. Depending on the purity requirements in this "sweating" process about 1 to about 70 wt %, often about 20 to about 50 wt %, of the crystallizate are melted again.

The liquid sweating fraction generated during sweating is removed by draining. Once the sweating is complete the temperature is increased to above the pure substance melting point and the remaining crystal layer is melted off.

The process according to the invention is performed in one or more crystallization stages. The crystallization stages may generally be divided into purification stages and stripping stages. To increase the separation efficiency a crystallization stage may be followed by further purification (crystallization) stages in which in each case the crystallizate of the preceding stage is crystallized. To increase the yield of the process, so-called stripping stages may be provided in which the liquid residue phase is subjected to stripping (crystallization) stages. This preferably proceeds according to the countercurrent principle where the crystallizate streams are supplied to the stages with the next highest stage number and the crystallization residue streams are supplied to the stages with the next lowest stage number. The number of crystallization stages and thus also of purification and stripping stages depends on the separation task and may be determined by one skilled in the art in the context of customary experiments.

The three fractions mother melt (residue), sweating fraction and molten crystallizate are generally charged into separate vessels, also referred to hereinafter as buffer vessels, via a distributor block. Depending on the process configuration residues and molten crystallizate are discharged from the process either as waste or as product of value or, when a plurality of crystallization stages are combined with one another, the fractions are passed into further stripping or purification stages. The sweating fraction generally has a very similar composition to the original feed composition and is therefore internally recycled, i.e. sent back to the crystallizer together with fresh feed in the following run.

According to the invention the optical rotation of at least the sweating fraction is determined online by means of a polarimeter. Particularly suitable therefor are process polarimeters operating according to the principle of magneto-optical compensation. Conventional polarimeters measure optical rotation via a mechanically rotated analyzer. The mechanical rotation leads to wear and gradually results in loss of measuring precision. The magneto-optical compensation measuring principle is based on the Faraday effect and does not require moving parts. A glass rod forming the core of a magnetic coil becomes optically active in proportion to a direct current flowing through the coil. The optical rotation of the process liquid is compensated by adjusting current and polarity.

The polarimeter may preferably be arranged in the discharge conduit of the melt crystallization apparatus for the melts generated in steps i) to iii). Alternatively, the polarimeter may also be installed in a bypass to the discharge conduit. It is further possible to install the polarimeter in the conduit from the distributor block to the sweating vessel instead of in the discharge conduit to the distributor block. However it is preferable when the valve block is arranged directly downstream of the polarimeter.

The changeover from step ii) to step iii) is controlled online by means of at least one control unit. The at least one control unit is preferably data-coupled to the polarimeter. This control unit is, in particular, a computer. The control unit generally controls a valve block that is located in the discharge conduit and is connected to the discharge conduit and to at least two buffer vessels for receiving the generated melts. The control unit controls the position of the valve (of the valves) which determine the discharging of the melt crystallization apparatus to the vessels for the melts generated in steps i) to iii). In addition, the control unit is in particular configured to control the temperature of the cooling surfaces of the melt crystallization apparatus. To this end the control apparatus preferably controls the coolant temperature.

In particular, in order to control the changeover from step ii) to step iii)
(a) a target value for the optical rotation of the sweating fraction is specified;
(b) a maximum permitted control difference of the actual value for the specific optical rotation from the target value for the optical rotation of the sweating fraction is specified;
(c) the actual value for the optical rotation of the sweating fraction is determined online or inline;
(d) the control unit effects the changeover from step ii) to step iii) not earlier than upon reaching the target value and not later than upon reaching the maximum permitted control difference of the actual value from the target value.

In a preferred embodiment the maximum deviation, i.e. the maximum permitted control difference of the actual value from the target value is not more than 0.3°, in particular not more than 0.2° and specifically not more than 0.15° optical rotation, for a length of the measuring cell of the polarimeter of 1 dm, a temperature of 25° C. and an employed wavelength of 589 nm. It is preferable when the actual value deviates from the target value by not more than 0.12%. When the process according to the invention is performed as a multistage process higher deviations from the target value can be tolerated in the first stage than in the second stage, the so-called product stage. In particular the maximum permitted control deviation of the actual value from the target value in the stage/stages before the product stage is not more than 0.3°, in particular not more than 0.2°, while in the last stage it is advantageous when the control deviation of the actual value from the target value is not more than 0.1°, in particular not more than 0.05° and specifically not more than 0.025°, in each case for a length of the measuring cell of the polarimeter of 1 dm, a temperature of 25'C and an employed wavelength of 589 nm.

The target value for optical rotation depends on the desired degree of optical purity in % EE (enantiomeric excess). Typically chosen for the optical rotation of the sweating fraction is a target value which corresponds to an EE value of at least 15% EE, in particular an EE value of at least 20% and, depending on the desired degree of purity or in the case of a multistage crystallization process depending on the crystallization stage, is generally in the range from 15% to 99.99% EE and in particular in the range from 20% to 99.9% EE. For a multistage crystallization, the target value for optical rotation will typically correspond to an EE value in the range from 95% to 99.99% EE and especially in the range from 98% to 99.9% EE in the last crystallization stage. Preferably, the control difference in EE units will be not more than 2% EE, in particular not more than 1% EE and especially not more than 0.5% EE.

In a suitable configuration the melt crystallization apparatus has a crystallization space having a feed for introduction of the melt(s) to be fractionated into the crystallization space, a temperature sensor for measuring the temperature of the melt(s) in the crystallization space and a temperature-control device for varying the temperature of the introduced molten enantiomer mixture and/or of the crystallizate partly formed therefrom, a discharge conduit which is closable with a valve and connected to the crystallization space and in which the polarimeter is located or with which the polarimeter is connected via a bypass conduit, optionally a temperature sensor located in the discharge conduit for measuring the temperature of the melt(s) in the discharge conduit;

a valve block that is located in the discharge conduit and is connected to the discharge conduit and to at least two vessels for receiving the generated melts and a control unit which is data-coupled to the temperature sensor, the polarimeter, the temperature-control device and a valve block and with which the temperature of the solid and liquid phases in the crystallization space and/or the valve block is controllable.

Figure 2:
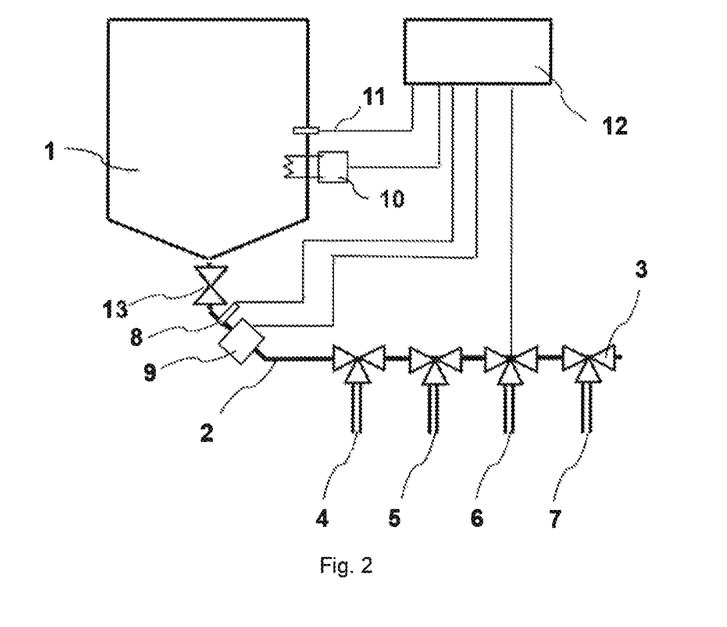

The invention further relates to a melt crystallization apparatus such as is exemplarily depicted in schematic form in FIG. 2 which has a space for the crystallization (1) having a feed (7) for introduction of the molten enantiomer mixture to be fractionated into the crystallization space (1), a temperature sensor (11) for measuring the temperature of the melt(s) in the crystallization space (1), and a temperature-control device (10) for varying the temperature of the introduced molten enantiomer mixture and of the crystallizate partly formed therefrom, wherein the melt crystallization apparatus further comprises a discharge conduit (2) which is closable with a valve (13) and connected to the crystallization space and in which a polarimeter (9) is located or with which the polarimeter (9) is connected via a bypass conduit, optionally a temperature sensor (8) located in the discharge conduit (2), preferably in spatial proximity to the polarimeter (9), for example upstream of the polarimeter (9), for measuring the temperature of the melt in the discharge conduit;

a valve block (6) that is located in the discharge conduit (2), preferably downstream of the polarimeter (9), and is connected to the discharge conduit (2) and to at least at least two buffer vessels (4), (6) for receiving the generated melts and optionally a further buffer vessel (5) for sweating fraction and has a control unit (12) which is data-coupled to the temperature sensors (8), (11), the polarimeter (9), the temperature-control device (10) and the valve block (3) and with which the temperature of the solid and liquid phases in the crystallization space and/or the valve block is controllable.

The enantiomer mixture to be fractionated generally does not have a racemic composition. In other words, an enantiomer-enriched enantiomer mixture serves as starting material for the process according to the invention. An enantiomer-enriched enantiomer mixture is to be understood as meaning mixtures in which the two enantiomers are not present in a 1:1 ratio. The enantiomeric excess required depends on the chemical nature of the enantiomer mixture to be fractionated. For conglomerate-forming systems the racemic composition has the lowest melting point. Purification by crystallization is therefore also possible in the case of low enantiomeric excesses in the starting mixture. For compound-forming systems the eutectic composition does not correspond to the racemate and a purification by crystallization is possible only when the starting mixture is enriched in one enantiomer in excess of the eutectic composition. Generally, a mixture of the enantiomers having an enantiomeric excess in one of the enantiomers of at least 10% EE (enantiomeric excess), in particular at least 12.5% EE and specifically at least 15% EE, for example in the range from 10% to 99.5% EE, in particular in the range from 12.5% to 99.0% EE and specifically in the range from 15% to 98.5% EE, will be employed for the crystallization.

The enantiomer mixtures to be fractionated according to the invention are in principle not subject to any limitations provided that they can form a eutectic mixture. One preferred application relates to mixtures of the enantiomers of a chiral terpene, in particular of a chiral mono terpene. Contemplated chiral monoterpenes include in particular camphor and isopulegol. Isopulegol is here to be understood as meaning the four possible diastereomers of isopulegol, namely n-isopulegol, isoisopulegol, neoisopulegol and neoisoisopulegol.

In a preferred embodiment the chiral monoterpene is isopulegol, in particular D/L-isopulegol. Generally, a mixture of D-isopulegol and L-isopulegol having an enantiomeric excess of one of the enantiomers of at least 10% EE (enantiomeric excess), in particular at least 12.5% EE and specifically at least 15% EE, for example in the range from 10% to 99.5% EE, in particular in the range from 12.5% to 99.0% EE and specifically in the range from 15% to 98.5% EE, will be employed as the enantiomer mixture to be fractionated.

In the context of a preferred embodiment the crystallization according to the invention is suitable for producing enantiomerically enriched L-(−)-n-isopulegol. Synthetic menthol is usually obtained via the intermediate L-(−)-n-isopulegol which differs from menthol only by a double bond in the isopropyl sidechain. Menthol is obtained therefrom by hydrogenation without loss of stereospecificity. L-(−)-n-isopulegol conforms to formula (M*)

wherein * in each case describes an asymmetric carbon atom in the absolute configuration depicted.

The present invention therefore relates to a process for producing menthol, comprising I) providing an isopulegol enriched in terms of the L- or D-enantiomer by a process described hereinabove and II) hydrogenating the isopulegol enriched in terms of the L- or D-enantiomer obtained in step I).

The invention is more particularly elucidated with reference to the appended drawings and the following examples.

Figure 1:
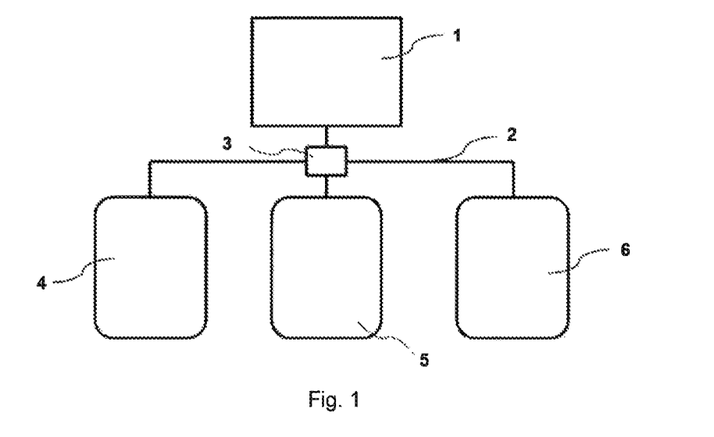

FIG. 1 is a schematic diagram of a melt crystallization apparatus. The apparatus comprises a crystallizer 1. The fractions from crystallizer 1 are divided among the buffering vessels for mother melt 4, sweating fraction 5 and molten crystallizate 6 via a discharge conduit 2 and subsequently via a valve block 3 comprising a plurality of valves.

FIG. 2 shows an exemplary embodiment for the integration of an online polarimeter into a static melt crystallization plant. The crystallizer 1 is connected to a valve/distributor block 3 via a discharge conduit 2 closable with valve 13. A temperature measuring means 8 and the online polarimeter 9 are located in the discharge conduit. In the valve/distributor block the stream from the crystallizer is distributed to the residue vessels 4 or the sweating fraction vessel 5 or the vessel for molten crystallizate 6. The feed is supplied to the crystallizer via conduit 7. A control unit 12 receives the signals from the temperature measurement and from the online polarimeter. The enantiomer ratio is determined from the measured temperature and rotation value via the calibration curve provided. Upon reaching the desired ratios the valves of the control unit are switched to pass the streams into the desired vessel. The control unit may furthermore be used to influence the temperature of the crystallizer 10 in order to further influence the EE value of the discharging sweating fraction for example. FIG. 2 depicts only one exemplary embodiment; the online polarimeter may continue to be installed in a bypass to the discharge conduit. It is further possible to install the polarimeter in the conduit from the distributor block to the sweating vessel instead of in the discharge conduit to the distributor block.

Figure 3:
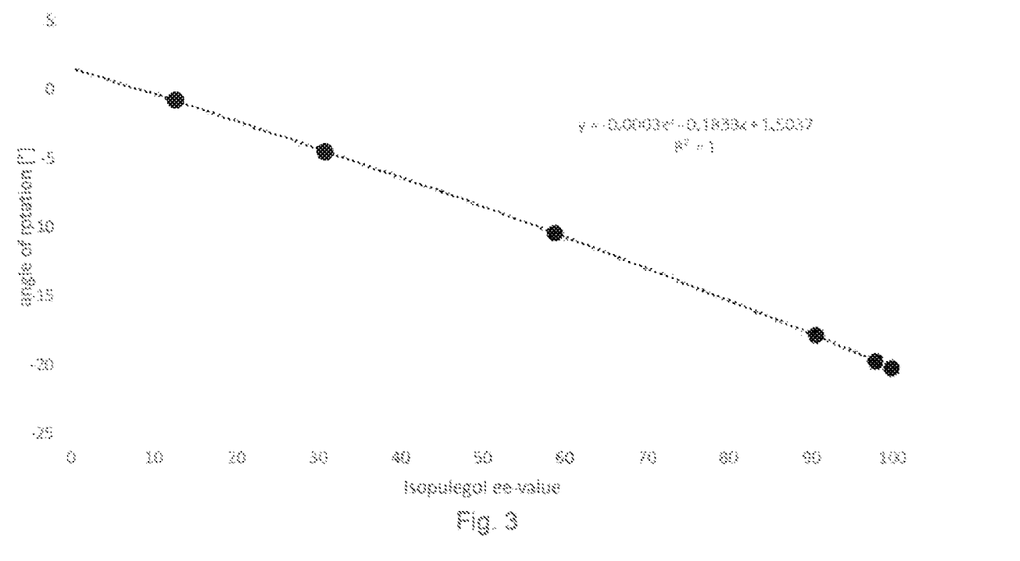

FIG. 3 shows a graphical plot of the rotation values as a function of the EE value for isopulegol.

Figure 4:
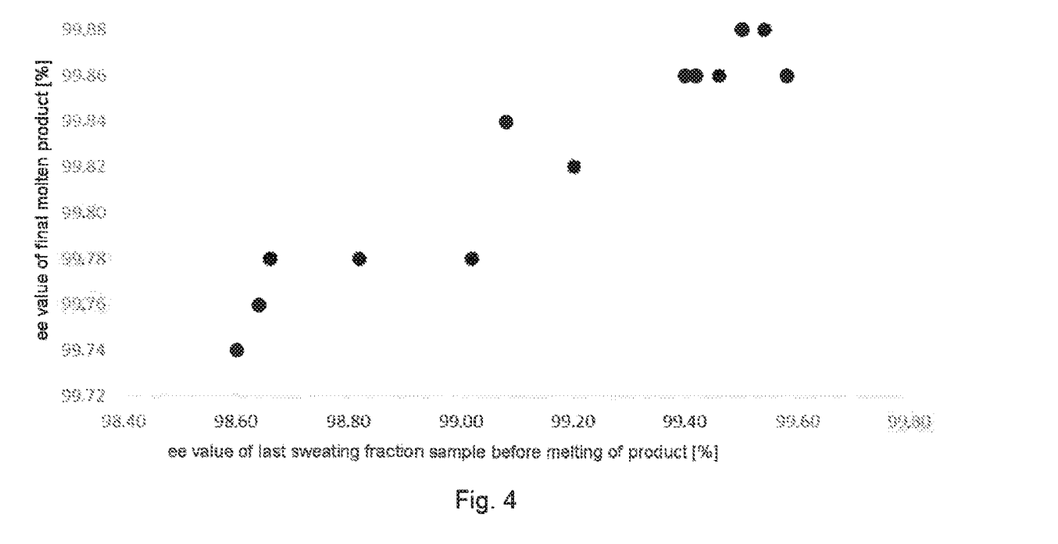

FIG. 4 shows a graphical plot of the EE value for the product as a function of the EE value for the last sweating sample.

Figure 5:
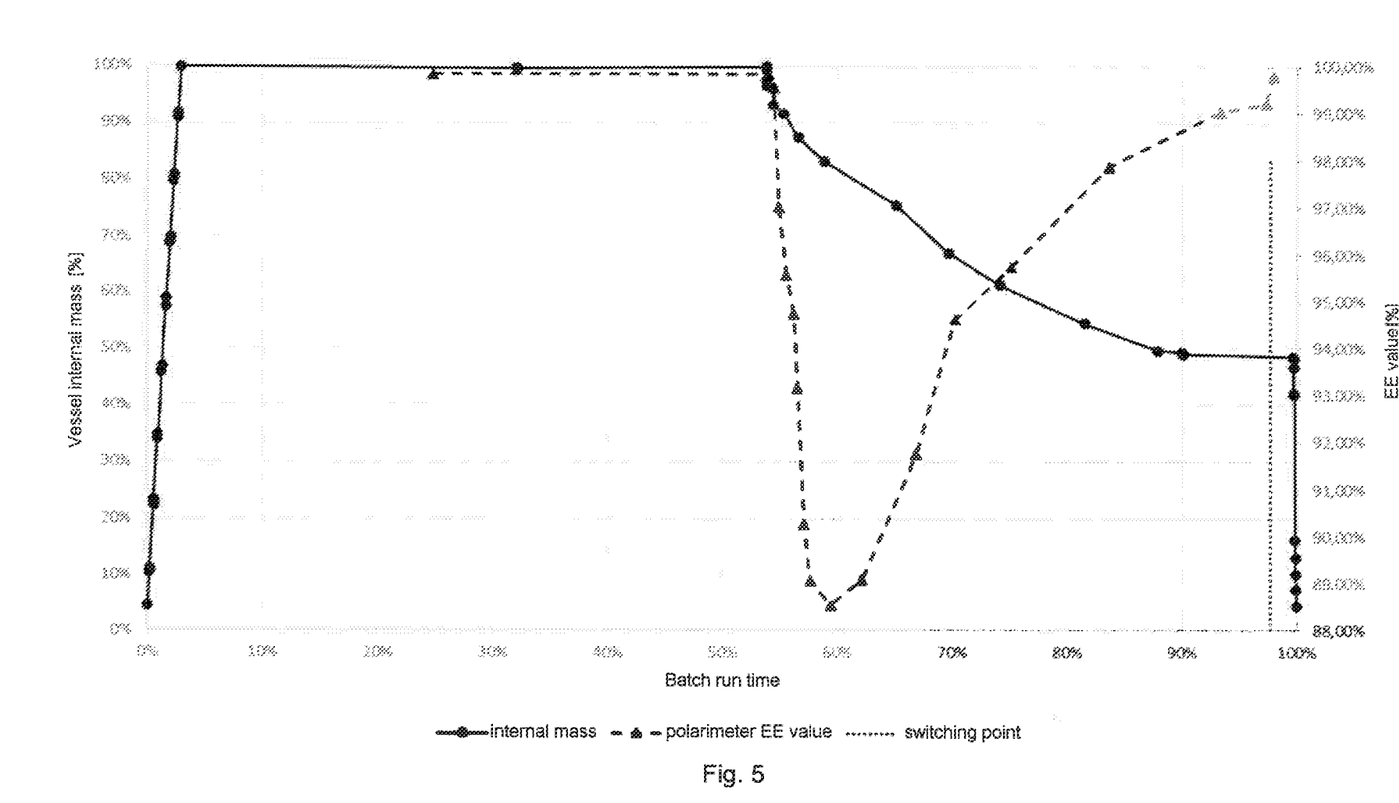

FIG. 5 shows the profile of the process according to the invention using the example of the last crystallization stage of a multistage batch crystallization of isopulegol in an apparatus according to FIG. 2, comprising the steps of crystallization, sweating and melting of the pure fraction. Plotted here is the profile over time of the relative proportion of the fill mass in the crystallizer (=% internal mass) and the profile over time of the EE value of the discharging isopulegol melt in EE % over the relative duration of the batch. The vertical dotted line indicates the time at which the valve to the sweating fraction vessel 5 is closed and from which the discharging melt is collected in the vessel for molten crystallizate 6.

EXAMPLE 1

Rotation value measurements were performed for the system L- and D-isopulegol. A Perkin Elmer model 343 polarimeter with a cuvette length of 100 mm and a light source having a wavelength of 589 nm was utilized. All measurements took place at a constant temperature of 25° C. First, the enantiomer ratio of L- and D-isopulegol in % EE was determined by gas chromatography. Table 1 reports the measured values for the rotation values as a function of the EE (excess of L-isopulegol).

TABLE 1

Measured values for the rotation value measurements for various enantiomer ratios of L- and D-isopulegol.

| % EE value | Optical rotation [°] |
| --- | --- |
| 12.56 | −0.82 |
| 30.84 | −4.522 |
| 58.8 | −10.42 |
| 90.6 | −17.77 |
| 97.88 | −19.66 |
| 99.84 | −20.17 |

FIG. 3 shows a graphical plot of the measured values from table 1. The measured values fit a 2nd order polynomial regression very well.

EXAMPLE 2

Operating data from the last crystallization stage of an industrial crystallization of L-isopulegol were evaluated. A melt crystallization apparatus according to FIG. 1 was used. Samples were taken from the discharging melt fraction passed into buffering vessel 5. The samples were analyzed online using a gas chromatograph. When the samples exceeded a certain minimum EE value the sweating was discontinued and the crystallizate was melted. Subsequently, this melt was passed into a vessel 6 (as per FIG. 1/FIG. 2) as a final product; a sample from the product stream was likewise taken and analyzed by gas chromatography.

Table 2 lists the measured EE values for the last sweating fraction sample and the molten product.

TABLE 2

| EE value for last sample of sweating fraction [%] | EE value for final molten product [%] | Feed EE value [%] | Relative mass of product based on original feed mass [%] |
| --- | --- | --- | --- |
| 99.54 | 99.88 | 97.7 | 46 |
| 99.46 | 99.86 | 97.6 | 46 |
| 99.58 | 99.86 | 97.5 | 46 |
| 99.20 | 99.82 | 97.4 | 47 |
| 99.42 | 99.86 | 97.3 | 46 |
| 99.50 | 99.88 | 97.3 | 45 |
| 99.40 | 99.86 | 97.2 | 47 |
| 99.02 | 99.78 | 97.1 | 51 |
| 98.60 | 99.74 | 97.1 | 53 |
| 98.64 | 99.76 | 97.4 | 53 |
| 98.82 | 99.78 | 97.6 | 54 |
| 98.66 | 99.78 | 97.8 | 54 |
| 99.08 | 99.84 | 98.3 | 51 |

FIG. 4 shows a graphical plot of the EE value for the product as a function of the EE value for the last sweating sample. A clear connection can be made between the EE value of the sweating sample and the EE value of the crystallizate. Depending on the desired purity of the product a minimum EE value of the last sample of the sweating fraction may be specified as a criterion for discontinuation.

The process according to the invention is also robust toward fluctuating starting EE values. Thus, table 2 also lists the feed EE value with which the crystallizer was originally charged. Despite fluctuating feed EE values the connection between the EE value of the sweating sample and the EE value of the crystallizate can be made.

The reference numerals used in FIGS. 1 and 2 are as follows:
1 Crystallization space
2 Discharge conduit
3 Valve block
4 Buffer vessel for generated (mother) melt
5 Buffer vessel for melt fraction
6 Buffer vessel for molten crystallizate
7 Feed conduit
8 Temperature sensor
9 Polarimeter
10 Temperature-control device
11 Temperature sensor
12 Control unit
13 Valve

The invention claimed is:
1. A process for enriching an enantiomer from an enantiomer mixture by a fractionating melt crystallization in a melt crystallization apparatus, comprising
   i) a crystallization step to obtain a crystallizate and a mother melt and removal of the mother melt from the crystallizate to afford a mother melt fraction,
   ii) sweating of the crystallizate obtained in step i) to afford a molten sweating fraction and a sweated crystallizate, and
   iii) subsequent melting of the sweated crystallizate to afford a molten crystallizate fraction, wherein the optical rotation at least of the sweating fraction is determined online using a polarimeter and the changeover from step ii) to step iii) is controlled online by means of at least one control unit.
2. The process according to claim 1, wherein in order to control the changeover from step ii) to step iii)
   (a) a target value for the optical rotation of the sweating fraction is specified;

(b) a maximum permitted control difference of the actual value from the target value for the optical rotation of the sweating fraction is specified;

(c) the actual value for the optical rotation of the sweating fraction is determined;

(d) the control unit effects the changeover from step ii) to step iii) not earlier than upon reaching the target value and not later than upon reaching the maximum permitted control difference of the actual value from the target value.

3. The process according to claim 2, wherein the maximum permitted control difference of the actual value from the target value is not more than 0.3° for a length of the measuring cell of the polarimeter of 1 dm, a temperature of 25° C. and an employed wavelength of 589 nm.

4. The process according to claim 1, wherein the melt crystallization apparatus comprises a discharge conduit for the melts generated in steps i) to iii) in which the polarimeter is located directly or with which the polarimeter is connected via a bypass conduit.

5. The process according to claim 4, wherein the control unit controls a valve block that is located in the discharge conduit and is connected to the discharge conduit and to at least two vessels for receiving the generated melts.

6. The process according to claim 1, wherein the melt crystallization apparatus has
a crystallization space having a feed for introduction of the molten enantiomer mixture to be fractionated into the crystallization space, a temperature sensor for measuring the temperature of the melt(s) in the crystallization space and a temperature-control device for varying the temperature of the introduced molten enantiomer mixture and/or of the crystallizate partly formed therefrom;
a discharge conduit which is closable with a valve and connected to the crystallization space and in which the polarimeter is located or with which the polarimeter is connected via a bypass conduit;
optionally a temperature sensor located in the discharge conduit for measuring the temperature of the melt(s) in the discharge conduit,
a valve block that is located in the discharge conduit and is connected to the discharge conduit and to at least two vessels for receiving the generated melts, and
a control unit which is data-coupled to the temperature sensor, the polarimeter, the temperature-control device and a valve block and with which the temperature of the solid and liquid phases in the crystallization space and/or the valve block is controllable.

7. The process according to claim 1, having at least one of the features x1) to x6):
x1) at least one control unit is preferably data-coupled to the polarimeter;
x2) the melt crystallization is performed as a layer crystallization;
x3) the melt crystallization is performed as a static layer crystallization on cooled surfaces;
x4) the melt crystallization is performed as a falling film crystallization;
x5) the enantiomer mixture to be fractionated does not have a racemic composition;
x6) the enantiomer mixture to be fractionated may form a racemic conglomerate.

8. The process according to claim 1, wherein the enantiomer mixture to be fractionated is a mixture of the enantiomers of a chiral terpene.

9. The process according to claim 8, wherein the chiral terpene is isopulegol.

10. The process according to claim 9, wherein a mixture of D-isopulegol and L-isopulegol having an enantiomeric excess of one of the enantiomers of at least 10% EE, is employed as the enantiomer mixture to be fractionated.

11. A melt crystallization apparatus having a crystallization space (1) having
a feed (7) for the molten enantiomer mixture to be fractionated into the crystallization space (1),
a temperature sensor (11) for measuring the temperature of the molten enantiomer mixture in the crystallization space (1),
and a temperature-control device (10) for varying the temperature of the introduced molten enantiomer mixture and of the crystallizate partly formed therefrom,
wherein the melt crystallization apparatus further comprises
a discharge conduit (2) which is closable with a valve (13) and connected to the crystallization space and in which a polarimeter (9) is located or with which the polarimeter (9) is connected via a bypass conduit,
optionally a temperature sensor (8) located in the discharge conduit (2), for measuring the temperature of the melt in the discharge conduit;
a valve block (3) that is located in the discharge conduit (2), and is connected to the discharge conduit (2) and to at least two buffer vessels (4), (6) for receiving the generated melts
and has a control unit (12) which is data-coupled to the temperature sensors (8), (11), the polarimeter (9), the temperature-control device (10) and the valve block (3) and with which the temperature of the solid and liquid phases in the crystallization space and/or the valve block is controllable.

12. The melt crystallization apparatus according to claim 11 which is configured as a falling film crystallizer or as a static layer crystallizer.

13. A process for producing an isopulegol enriched in terms of the L- or D-enantiomer, comprising a fractionating melt crystallization of a non-racemic mixture of the D- and L-enantiomers of isopulegol according to claim 1.

14. The process according to claim 13, wherein a mixture of D-isopulegol and L-isopulegol having an enantiomeric excess of one of the enantiomers of at least 10% EE is employed.

15. A process for producing menthol, comprising
I) providing an isopulegol enriched in terms of the L- or D-enantiomer by a process according to claim 13 and
II) hydrogenating the isopulegol enriched in terms of the L- or D-enantiomer obtained in step I).

16. The process according to claim 13, wherein a mixture of D-isopulegol and L-isopulegol having an enantiomeric excess of one of the enantiomers in the range of 12.5% EE to 99% EE, is employed.

17. The process according to claim 1, wherein the enantiomer mixture to be fractionated is a mixture of the enantiomers of a chiral monoterpene.

18. The process according to claim 17, wherein the chiral monoterpene is D/L-isopulegol.

19. The process according to claim 9, wherein a mixture of D-isopulegol and L-isopulegol having an enantiomeric excess of one of the enantiomers is in the range from 12.5% EE to 99% EE, is employed as the enantiomer mixture to be fractionated.

20. A melt crystallization apparatus having a crystallization space (1) having a feed (7) for the molten enantiomer mixture to be fractionated into the crystallization space (1), a temperature sensor (11) for measuring the temperature of the molten enantiomer mixture in the crystallization space (1), and a temperature-control device (10) for varying the temperature of the introduced molten enantiomer mixture and of the crystallizate partly formed therefrom, wherein the melt crystallization apparatus further comprises a discharge conduit (2) which is closable with a valve (13) and connected to the crystallization space and in which a polarimeter (9) is located or with which the polarimeter (9) is connected via a bypass conduit, optionally a temperature sensor (8) located in the discharge conduit (2), in spatial proximity to the polarimeter (9), for measuring the temperature of the melt in the discharge conduit;

a valve block (3) that is located in the discharge conduit (2), downstream of the polarimeter (9), and is connected to the discharge conduit (2) and to at least two buffer vessels (4), (6) for receiving the generated melts and has a control unit (12) which is data-coupled to the temperature sensors (8), (11), the polarimeter (9), the temperature-control device (10) and the valve block (3) and with which the temperature of the solid and liquid phases in the crystallization space and/or the valve block is controllable.

\* \* \* \* \*